United States Patent
Weber et al.

(10) Patent No.: US 6,440,121 B1
(45) Date of Patent: Aug. 27, 2002

(54) SURGICAL DEVICE FOR PERFORMING FACE-LIFTING SURGERY USING RADIOFREQUENCY ENERGY

(75) Inventors: Paul J. Weber, Fort Lauderdale, FL (US); Luiz B. Da Silva, Danville, CA (US); Michael Robert Weber, Palm Harbor, FL (US)

(73) Assignee: Pearl Technology Holdings, LLC., Tampa, FL (US)

( * ) Notice: Subject to any disclaimer, the term of this patent is extended or adjusted under 35 U.S.C. 154(b) by 0 days.

(21) Appl. No.: 09/475,635

(22) Filed: Dec. 30, 1999

Related U.S. Application Data

(63) Continuation-in-part of application No. 09/085,948, filed on May 28, 1998, now Pat. No. 6,203,540.

(51) Int. Cl.⁷ ............................................. A61B 18/18
(52) U.S. Cl. .................................. 606/2; 606/9; 606/13
(58) Field of Search .............................. 606/2–4, 9–11, 606/13, 15, 16, 27, 28, 32, 34, 40, 41, 49, 169; 604/22, 35, 19; 601/2

(56) References Cited

U.S. PATENT DOCUMENTS

| | | | | |
|---|---|---|---|---|
| 5,733,319 A | * | 3/1998 | Neilson et al. | 607/105 |
| 5,759,182 A | * | 6/1998 | Varney et al. | 606/21 |
| 6,033,398 A | * | 3/2000 | Farley et al. | 606/27 |
| 6,210,405 B1 | * | 4/2001 | Goble et al. | 606/41 |

OTHER PUBLICATIONS

P.J. Weber et al., Bulbous–Lysing Underminers, J. Dermatol Surg. Oncol., 15:12, Dec. 1989, pp. 1252–1253.

* cited by examiner

*Primary Examiner*—Michael Peffley
(74) *Attorney, Agent, or Firm*—John P. Wooldridge

(57) ABSTRACT

The human face is efficiently and precisely dissected while radioifrequency energy is applied to controllably release target tissue bonds and alter surrounding tissues in such a fashion that these facial tissues contract and tighten in response to the energy application while automatically excluding vital nerves and vessels. Tightening will be most dramatic in younger patients between 45 and 55 years of age such that the surgeon may not have to cut-out or stretch skin for a desirable effect in most of this population. The device is inserted through only 3 relatively small 1 cm incisions allowing energy to be applied to the upper subcutaneous, lower dermal and platysmal face-lift layers. The procedures take less than 15 minutes following anesthesia and the effects will last for at least several years. The special arrangement of protrusions and recessions on the tip of the instrument allows the surgeon to efficiently force the device through face-lift planes with instantaneous knowledge of the location and progress simply by the "feel" of the apparatus. Vibrational energy and optional ultrasonic means will yield speed enhancement and tip debris and char reduction. The device and method permit efficient tissue separation and alteration of the lower face-neck-unit tissues, mid-face-unit tissues and scalp-forehead-temple-unit tissues.

32 Claims, 3 Drawing Sheets

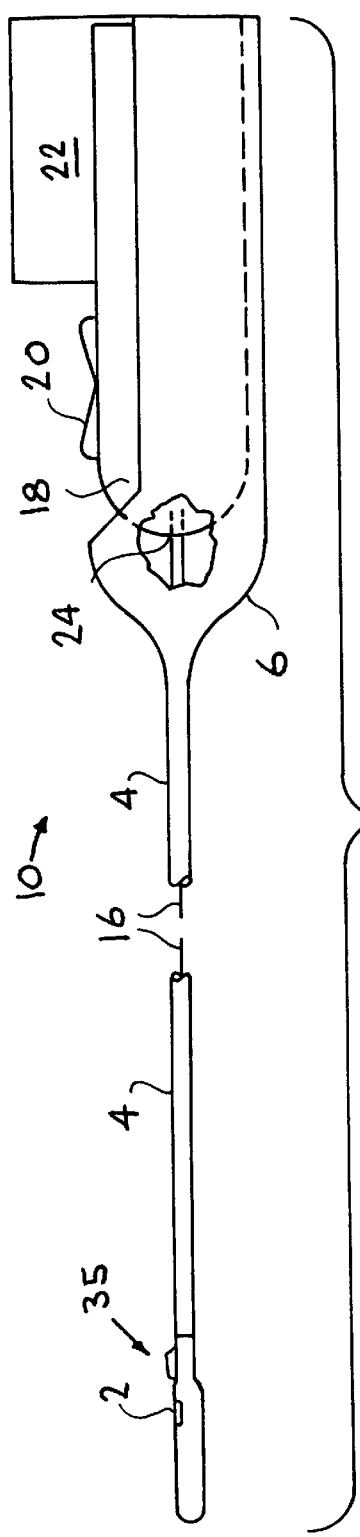
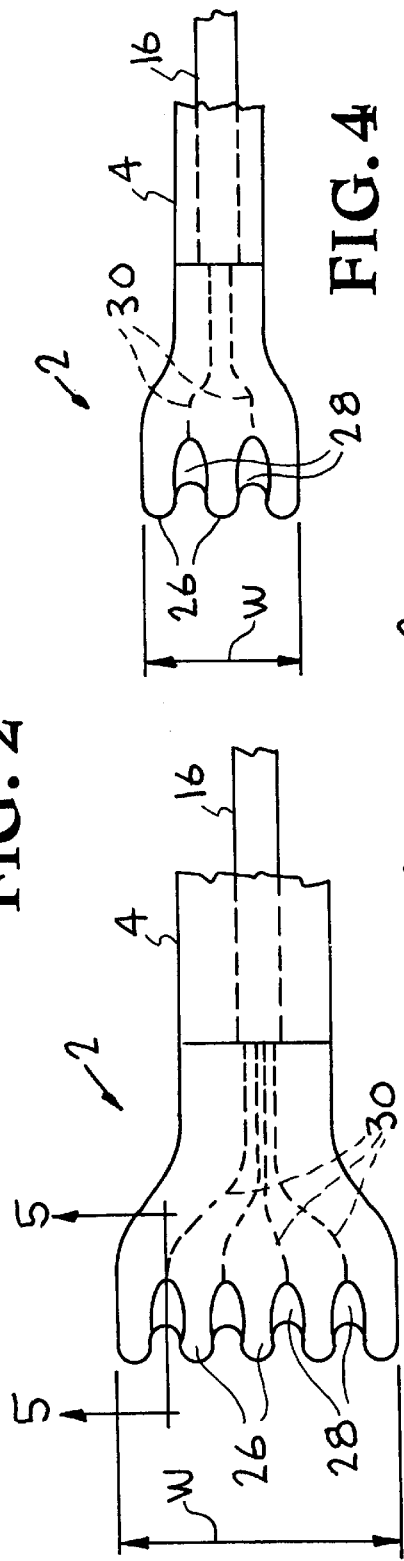
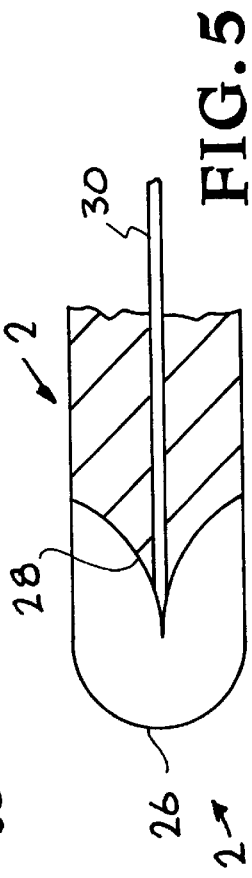

SURGICAL DEVICE FOR PERFORMING FACE-LIFTING SURGERY USING RADIOFREQUENCY ENERGY

This application is a continuation-in-part of U.S. patent application Ser. No. 09/085,948, filed May 28, 1998, now U.S. Pat. No. 6,203,540.

BACKGROUND OF THE INVENTION

1. Field of the Invention

This invention relates to a surgical device for performing face-lifting surgery using electromagnetic radiation, and more particularly to a device with a specialized tip design that delivers radiofrequency energy and optional ultrasonic energy application. More particularly, the invention provides a surgical device that can improve the accuracy and speed of face-lift operations. Use of the present invention may controllably cause thermally related healing contraction of the target tissues thus allowing face lifting in younger patients without the removal or cutting-out of skin.

2. Description of Related Art

Critical Anatomy and Nomenclature

Definitions

Cutting (in surgery) will be defined as relatively cleanly breaking through similar or dissimilar tissues with minimal adjacent tissue trauma and thus little tissue stretching, tearing or ripping.

Lysis (in surgery) will be defined as breaking through similar or dissimilar tissues with or without adjacent tissue trauma and may involve stretching, tearing or ripping. Depending upon the tissues lysed, the degree of stretching or tearing of lysed tissue edges may be inconsequential or may even result in a desirable benefit such as post surgical contraction.

Planes of tissue are not often flat and represent the curviform intersection of dissimilar tissues and are made at least partly of fibrous tissues, either loose and spongy or firm and tough. Planes between the soft internal organs are usually loose and spongy. Planes of tissues in the face and on bones are firm and tough.

Undermining will be defined as tissue separation either within or between defined tissue planes. Surgically speaking, undermining may be "sharp" (instrument) or "blunt" (instrument) depending upon the amount of fibrous tissue binding or existing between the tissue planes to be separated. Undermining is usually performed, as is most surgery, with the intention of minimizing trauma. Sharp instrument undermining is usually performed to separate highly fibrous or collagenous tissues, however sharp undermining suffers from the risk of penetrating adjacent tissues inadvertently because of loss of ability to follow the desired plane. Inability to follow or maintain the plane in sharp undermining is frequently due to limited visibility, difficulty "feeling" the fibrous plane, or scarring (collagen fibrosis) resulting from previous trauma or surgery. Even experienced surgeons lose the correct plane of sharp undermining; great skill is required. Blunt undermining allows a rounded, non-sharp tipped, instrument or even human finger to find the path of least resistance between tissues; once the desired plane is found by the surgeon it is easy to maintain the plane of blunt undermining until the task is complete. Unfortunately, blunt undermining between highly fibrous tissues such as the human face usually causes tunneling with thick fibrous walls.

Dissection usually implies sorting out and identification of tissues and usually implies that some sort of undermining has been performed to isolate the desired structure(s). In face-lifting surgery, plastic surgeons have so commonly used the terms undermining and dissection interchangeably that they have become synonymous in this specific situation.

Tracking means to maintain a direction of movement upon forcing a tissue separating without unpredictable movement or leaving the desired tissue plane(s).

Planar tracking means to stay in the same tissue planes.

Linear tracking means to move uniformly in a straight or uniformly curved path without unpredictable movement. Groups of linear tracks may form a network that creates an undermined tissue plane.

Anatomical Perspective: Lysis or undermining in one dimension (linear=x) implies forming a tunnel. Lysing or undermining in 2 dimensions at any one instant forms a plane (x,y). Traditional face-lift undermining is done just under the leather (dermis) layer of the skin where dermis joins underlying fat (or subcutaneous, "SQ"). Even deeper within the SQ fat run larger blood vessels and delicate, non-regenerating motor nerves to the muscles that give the human face motion and expression. Deep/beneath to the SQ fat reside the muscles and glands of the face. The relevant face-lift anatomy may be referenced in {Micheli-Pellegrini V. Surgical Anatomy and Dynamics in Face Lifts. Facial Plastic Surgery. 1992:8:1–10. and Gosain A K et al. Surgical Anatomy of the SMAS: a reinvestigation. Plast Reconstr Surg. 1993: 92:1254–1263. and Jost G, Lamouche G. SMAS in rhytidectomy. Aesthetic Plast Surg 6:69, 1982.} The SQ fat differs from body location to body location. On the face, the SQ fat has many fiber-bundles (septae) carrying nerves and blood vessels. If a surgeon were to move, shove, or forwardly-push a blunt, dull-tipped, 1-inch chisel or pencil shaped device through the fat of the face where SQ abuts the dermis, the sheer thickness of the fiber bundles would likely cause slippage of the device and result in the formation of pockets or tunnels surrounded by compacted fiber bundles or septae. Proper performance of a face-lift involves breaking the septae at a proper level to avoid damaging more important structures such as blood vessels and nerves and glands.

Disadvantages of the current techniques are numerous. Face-lifting devices described in the prior art resemble undermining devices that were constructed with cutting edges that rely entirely on the skill of the surgeon to maintain control. Inadvertent lateral cutting or tissue trauma may be difficult to control. In addition, speed of separation is effected to ensure accuracy by the surgeon in separating fibrous tissue planes. There are two principle locations for face lift undermining (dissection): in the more common lower facelift (cheek/neck-lift) undermining in the subcutaneous tissues is customarily performed; in the less common upper facelift (which approximates brow-lifting) undermining in the subgaleal or temporalis fascia plane is customarily performed. Use of prior art undermining devices (including scissors, sharp rhytisectors, etc) in these planes during cosmetic surgery has, at times, resulted in unwanted cutting, trauma or perforation of adjacent structures. Scissors and rhytisectors are planar cutting instruments and thus the position of the cutting edges with respect to the surface of the face is controllable only by the surgeon estimating location as no $3^{rd}$ dimensional bulbous limitation exists. Unfortunately, scissors with 3 dimensionally "bulbous", rounded tips can not close all the way to cut target tissue. Scissors with 2 dimensionally rounded tips can close all the way to cut target tissue but may wander inadvertently between tissue planes due to the thin third dimension (thickness) of the scissors blades.

Current face-lifting instruments that cut with other than manual energy do not address the novel concept of a "protected plane" during energized face-lifting dissection. Current lasers must be fired from positions that are external to or outside of the patient to energize limited pockets of tissue within the face and unfortunately affect target tissues in a very imprecise fashion (reference: in *Manual of Tumescent Liposculpture and Laser Cosmetic Surgery* by Cook R C and Cook K K, Lippincott, Williams, and Wilkins, Philadelphia ISBN: 0-7817-1987-9.). Target tissue is altered with relatively little control in current laser-face lifting techniques. Current electrosurgical devices for face-lift tissue energizing must be delivered through large cut open pockets of skin (flaps) or through the limited access and slow moving, tedious endoscopes. It would be advantageous to provide a safe harbor for the precise application of energy to proper face-lift tissues to be separated and energized while excluding vital structures such as nerves and delicate vessels and maintaining an exact distance from the very delicate surface of the skin. It would be additionally advantageous for the same provisions to allow for a uniform forward tracking and feel of motion of the device that provides a surgeon with instantaneous knowledge. Properly sized and placed protrusions and recessions address all of these problems in a manner not previously possible.

Other disadvantages of the current techniques are described in the following. One of the most recent competing procedures to incompletely dissect/lyse/cut a face-lift plane is traditional or ultrasonic liposuction. Unfortunately, dissection is incomplete as the cannulas only make tunnels. The tissues between the tunnels must be cut with scissors in order to create a plane. When the scissors cuts the fiber tissues and blood vessels constituting the walls of the tunnels, bleeding and trauma occur and frequently require spot coagulation under visualization. Other severe drawbacks of the incomplete undermining that liposuction cannulas perform is the common trauma and resultant mouth droop paralysis that occurs in the hands of even prominent surgeons when the delicate and anatomically unpredictable (20% of the population) marginal mandibular nerve is cut. Additionally, ultrasonic cannulas become hot and can cause thermal burns called "end hits" when the cannula tip is thrust against the inside of the skin as is common during the procedure.

Just as sharp undermining or dissection has its disadvantages, as previously mentioned, blunt dissection suffers from its own difficulties as well. Forcing a blunt object through tissue avoids indiscriminate sharp cutting of important structures (nerves, vessels). Blunt undermining compacts the stronger, firmer, strands of collagen contained within even tissues as soft fat into thicker "bands" (some overly thick for uniform cutting). Undesirably for a face-lift, blunt object undermining will force aside and compact septae causing incomplete lysis or freeing of the tissues. Also unfortunately for face-lifting, purely blunt object undermining will result in the indiscriminate/random motion/uncontrollable-slippage of the underminer tip and thusly the underminer through target tissue.

Currently it takes surgeons between 20 minutes and one hour to dissect/undermine/lyse/lift a lower face. It usually takes between 10 minutes and 30 minutes, depending upon the patient to spot coagulate/seal all of the blood vessels that were cut during the aforementioned lysing portion of the face-lift. For upper face-lifting times are less than half that mentioned for lower face-lifting. The present invention would reduce time for a surgeon to do both the duties of lysing and coagulation since the device performs both tasks as well as keeps perfect positioning and tracking. The time reduction should be at least 50–75%. Reduced operating time means less time a wound is open to potential infection, lowered surgical costs and less time under anesthesia and thus a general improvement in the procedure.

There exists a special subset of the general population that may benefit uniquely from the present invention. Men and women between the ages of 45 and 55 are just beginning to droop and develop folds. However, there is not much undulating wrinkling as in older patients. Currently long incisions of 10–20 cm are made around each of the two ears, for the purposes of hiding the scars. Skin is cut out and discarded and the remaining skin stretched. Skin does not thicken in response to stretching it only thins. Unfortunately, some plastic surgeons in the early 1990's advocated "prophylactic" or "preemptive" face-lifting on women in their 40's purportedly to "stay ahead of nature." This philosophy has been discounted and discredited by the vast majority of reputable experts. With the present invention tightening will be most dramatic in younger patients between 45 and 55 years of age such that surgeons may not have to cut-out or stretch skin for a desirable effect for most patients in this population. In this case, the present invention is inserted through only 3 relatively small incisions of less than 1 cm each and energy is applied to the upper subcutaneous, lower dermal and platysmal face-lift layers. If the 3 small incisions can be used and no skin excised then the procedure will take less than 15 minutes following anesthesia and the effects will last for at least several years.

The present invention was made in light of such deficiencies of the prior art.

It is, therefore, an object of the present invention to provide an undermining device that can position lysing surfaces at a proper level for fibrous tissue lysing during a face-lift. It is a further object of the invention to provide quick and accurate face-lifting maneuvers. It is yet a further object of the invention to provide a surgical face-lifting device that easily maintains the proper dissection plane. Additionally, it has been shown that thermal effects to the collagenous (dermal, superficial platysma musculature and other) tissues of the face in the facelift plane can cause cosmetically desirable contraction of the dermal tissues with beneficial tightening of the facial tissues.

Laser derived thermal damage/change to the collagenous (dermal, superficial platysma musculature and other) tissues of the face in the facelift plane can cause cosmetically desirable contraction with beneficial tightening of the facial tissues has been documented in *Manual of Tumescent Liposculpture and Laser Cosmetic Surgery* by Cook R C and Cook K K, Lippincott, Williams, and Wilkins, Philadelphia ISBN: 0-7817-1987-9. It can be deduced that similar thermal effects derived from radiofrequency devices can also cause similar changes.

The disclosures of this publication and the disclosures of all other publications recited herein are incorporated by reference as if fully set forth herein.

Rubin (U.S. Pat. No. 3,667,470) and Hendel (U.S. Pat. No. 4,600,005) refer to devices that are used to plane down grooves in bone, through bone and the junction of bone and its surface covering. Bony tissue and its response to guided shearing and chiseling is totally different than the dynamics involved in creating a plane through the fibers of one of the softer tissues of the body (SQ fat) and the dermis, a moderately density tissue. Another major difference is that bone is immobile and not cut-able with a knife or scissors. Fat and dermis of the face wobble and move around (mobile) when being worked upon; fat and dermis can be cut by knife and scissors. For traditional face-lifting fat and dermis would need to be specially stabilized during manipulation or cutting or planing and are penetrable (or subject to damage) by instruments that would be used to cut, manipulate, harvest, or alter bone such as Rubin and Hendel. The present invention is able to stabilize the mobile tissues of the face for proper undermining during a face-lift.

Rubin teaches a "bone shaver and groover" and shows in a diagram a single sharp edged extension protruding perpendicular to the plane of motion of the cutting edge of the device. The extension is intended to carve and maintain a groove in rigid, immobile, bone as it is pounded forward by a surgeon's hammer. The extension rips a canal in the rigid, rock-like bone as it strips along the surface of the bone. This is not such a problem in bone because bone has very little blood supply or nerves to damage or destroy. The facial tissues, especially the junction where the fat meets the dermis is the exact opposite situation with plenty of delicate nerves and blood vessels that would be ruptured and irreparably damaged with a device such as Rubin. The Rubin differs from the present invention in the direction of intended motion. Rubin would not work in the tissues where the present invention would work and would simply tear vessels and cause bleeding and injury to tissues. Tracking would not be maintained because the Rubin extension could not maintain a track in softer tissues with an irregular fibrous nature such as the face. Additionally, since the extension would be ineffective, even if multiple in number, Rubin would slip during forward motion causing the difficulties mentioned previously in soft tissue undermining with a blunt object with no tracking.

Hendel teaches a "guided osteotome for harvesting cranial bone graft" the entire cutting tip between the edges is sharp and the device would cause extensive bleeding in non-bony tissue separation. However, Hendel does use rounded, bulb-like "guides" at the edges of the skull bone harvesting instrument yet the guides are only two in number and are spaced 20 mm or 2 cm apart. The guides prevent the hammer driven cutting edge from penetrating the skull too deeply as the harvesting cutting edge would tend to "dive" deep into the skull toward brain tissue if unhindered (vertical tracking control). Hendel differs from the present invention in which protrusions function to compress the collagenous, fibrous tissues into recessions making for a more precise lysis of the grouped fibers and bundles. Hendel also refers to his "guides" as skids and that is just what happens. Horizontal tracking is not controlled by the skids as the name suggests and the surgeon has to control horizontal tracking across the skull by hand control on the fulcrum of the wood-chisel-like device. The present invention and protuberances/bulbs differ being greater than two per device and allowing for forward motion with BOTH vertical and horizontal tracking.

The references to follow relate to energized surgical tools that perform mostly destructive functions but only have the potential to inefficiently cut an extremely limited plane within human tissue for face-lifting purposes.

Farin (U.S. Pat. No. 5,776,092) works analogously to a three-color ballpoint "click-pen." Farin is composed of only one laser, one ultrasound, or one-two radio frequency devices, hidden inside a "deliverable" tube. The Farin deliverable tube could never be forced against the more fibrous tissues of the face-lifting plane. Farin would catch, tear, or puncture the tissue and could not "find" or "separate" or "create" a plane. Farin basically acts, as can be seen diagrammatically, as a stationary point of application of energy. The immobility limitation was mentioned numerous times by Farin in the patent such that: a scope/monitor/scanner must be used in order to find out where the device is and whether it is being properly activated. Farin could not be used to radially undermine a facelift in any efficient fashion. It would literally take hours for the point-like device of Farin to do the task of a facelift, because visualization of every area of damage/tissue alteration would need to be maintained on a constant basis. In fact, in column 1, Farin cites endoscopic operation use in no less than three lines. In column 2, Farin teaches treatment tips that have to be withdrawn into the device, in order to hide and clean the tips (as opposed to the present invention which is self-cleaning and therefore exposed at all times). Farin admits that coagulated tissue unfortunately adheres to Farin because of its tendency to catch debris in the design shown and to hinder or make ultrasound dissection impossible. In column 3, line 2, Farin discusses that the RF-applicator can push out from the target tissue, allowing the laser to be better focused. Farin intimation that force is not applied to move this device forward, and that this is a relatively stationary device. To actually target the laser using one of the probes to force target tissue gradually to the focal length of the laser implies the limited movement capabilities of this device. Farin further, in claim 1, mentions that Farin is only longitudinally movable within its housing for retraction or extension, which is necessary to help keep the tips clean, so that they are not to "catch" on tissue. Farin, from this comment, admits that the device could not efficiently move through the extensive fibrous tissue connections necessary to be lysed in a clean or uniform fashion for a facelift in any reasonable amount of surgical time. Farin in claim 10 mentions only the lateral spacing of the various energy tips, because they must be located side by side within this very limited device which contains only one or two tips (as opposed to the present invention that is rigidly and laterally alternating and fixed). Farin device would be impractical in its present form to carry more tips, as a multiplicity would simply increase the effective diameter of the device and limit its ability to migrate within tissues to the target site. Farin was aware that there would be no advantage of having additional energy sources, unless the tips were constantly becoming dirty during the procedure. Farin, in claim 11, again mentions the "controller for automatically adjusting the longitudinal position." In claim 11, Farin refers to a device function very similar to a three-color ballpoint pen, which has a click in and out to change ink color choice. In claim 14, Farin describes tips, rotate-able like a Gatling gun, in order to permit successive use of clean tips inside and outside of the housing. Farin is basically a limited-mobility-hiding-shell mimicking the less traumatic features of a feminine-hygiene product dispenser. Farin is limited and can only deliver the energy sources to a small spot for localized treatment and destruction, but would be incapable of efficient or widespread plane undermining necessary for face-lifting. Farin implies that differing types of energy need to be applied alternately to the tissue being treated. In summary, Farin has no efficient radial motion capability; Farin is relatively immobile while energizing/altering target tissue; Farin has no appreciable speed of motion with simultaneous energizing; Farin has a different shape impractical for face-lifting.

Kittrell differs significantly from the present invention. First and foremost, Kittrell is a laser energized device. Secondly, Kittrell it is a catheter capable only of working inside delicate blood vessels. Kittrell is very similar to Farin in basic smoothness, and non-rigidity. Kittrell migrates linearly along the path, in this case, into a blood vessel in order to destroy coronary artery plaques. Kittrell describes numerous embodiments in all of which multiple laser fibers are carried down a catheter. These laser devices are ingeniously aligned to touch the catheter (catheters are bendable/deformable/floppy as opposed to the present invention that is rigid and fixed) tip in a special fashion so that laser light comes out to destroy plaques on the proper side of the vessel. Kittrell provides for placing balloons, spacers, and other materials around the tip. These are non-rigid, of course, since anything rigid applied with even slight force into a blood vessel could puncture the vessel and cause tissue death. Kittrel is completely different from the present invention. The present invention relies on force through tissue under extreme pressure, in order to subject target tissue under high pressure in the recessed zones between the larger bulbous protrusions. Kittrell claims an internal array of fibers, showing how numerous fibers would need to be packed if they are to reach a tip in a beneficially packed array. Numbers that pack appropriately, according to Kittrell, are 19, 61, etc. Kittrell is basically just a laser catheter, not meant for hard shoving, sweeping, probing, undermining or lifting. Kittrel is a catheter that delivers a destructive force only at the tip functioning only after slow, meticulous cautious placement/motion. Kittrell proposes one or multiple fiberoptic laser carrying tubules in position to fire against the tip of the catheter and, thus, affect the target plaque. Again, Kittrel is a soft and delicate singular device, in no way related to the present invention (in which compressive mechanisms and way of forcing the device through the tissue are largely dependent upon the design and dynamics of the tip). In FIG. 17B, Kittrel shows a somewhat flattened array of lasers firing, but these could not undermine or "lift" a face or carry energy sufficient to damage tissue uniformly. All of the laser tips within Kittrell device take place within an area of uniform external/outside curvature and instrument-tissue-energy transfer does not occur, as in the present invention, in areas of alternating recessions. Kittrell in FIG. 17D shows a flattened array of lasers, but, nevertheless, there are no finger-like protrusions/projections, with lasers prominent and lysing recessions between. Without the grooved tracking tip it is not possible to prevent slippage from a uniform plane for a facelift without visualization. A liposuction cannula would be vastly superior to Kittrell separating and treating facelift tissue. Unfortunately a liposuction cannula would leave many disconnected fibrous tissue tunnels in the face instead of establishing a totally connected plane of separation.

Kittrell and Farin both share dissimilarities with the present invention. In Kittrell, column 1, line 53–63, the preferred embodiment requires a fiberoptic viewing bundle. Thus, visualization is necessary in Kittrell, and even preferred. In column 4 Kittrell states that the protective shield is singular in nature and that the numerous filaments, fibers, or other laser energy-carrying devices are contained within that entire shield. This differs from the present invention, wherein there are numerous protrusions acting as shields allowing tissue compression to take place between. Thus, lysing of the pre-selected target tissues is possible when compressed in those intervening segments. Kittrell, in column 8, lines 19 through 25, again discusses the linear array. In this case the linear array is simply the efficient circumferential packing of fibers within a circular tubule, totally different from the most important energy applying area described in the present invention, which is virtually linear or slightly arciform if anything. The energy application of Kittrell is completely based upon a spherical distribution of potential laser energy excitation sources and is not capable of any useful dissection in a planar fashion for face-lifting. The bulk of Kittrell is concerned with the circumferential or linear array pattern that is re-emphasized in column 12, numbers 19, 37, and 61, describing the most efficient packings for fibers in a tubular structure in a linear array. In column 14, lines 40–60, Kittrel indicates the necessity for guide catheters, x-ray scans, or endoscopic visualization; this highlights the requirement for some type of visualization for its best and intended use. Again, Kittrell would be an extremely poor (if not impossible) method for undermining planar fibrous tissues, such as a face-lift. Kittrell treats a relatively fixed target in one or several locations. No force is to be applied upon Kittrel in order to gain separation.

In summary, Kittrell is not capable of planar separation, Kittrel's device requires visualization, Kittrell does not permit the kinetic stripping of tissues. In column 25, lines 35–40, Kittrell states said working regions must be a cross-sectional area just large enough to allow catheter passage, but not much larger than that. Also in column 26, lines 35–40, Kittrell prefers a geometrically expanding pattern of energy distribution around a beam axis. This is the opposite of what is desired primarily in the present invention. Concentrated energy will aid the lysing action. However, a diffuse energy spread may also be a helpful byproduct by slowing bleeding and diffusely shrinking collagen. In column 28, Kittrell re-emphasizes that laser is used to destroy an observed blockage or obstruction. Kittrel is diametrically opposed to the present invention, which is basically used to alter, or change, tissue without its complete destruction, primarily seeking separation and shrinkage.

Broadwin (U.S. Pat. No. 5,015,227) is an extension of Farin (except that Farin is a probe that is manipulable with recommended visualization). Broadwin would become caught and its movement impeded by hanging-up in the fibrous tissues of the face. Broadwin has an intended use for pinpoint (x) tissue fragmentation hemostasis. Broadwin would not be able to efficiently undermine or cut a semi-fibrous tissue plane (x,y) as is necessary in a facelift. The ultrasonic transmission in Broadwin also differs from the present invention. In Broadwin ultrasound occurs in a central pinpoint area around a radio frequency device, as opposed to having the entire device ultrasonically vibrate as in the present invention. Broadwin does not make use of the focused ultrasonic energy in the lysing/recessed/thinner segments, as the present invention does. The present invention works on the principles that ultrasonic energy would concentrate in the recessions and magnify the effects of other existing energies in these locations, as the device is forced by the surgeon's arm energy against the dermal fibers to be lysed. This principle is the main physical basis of the physical characteristics of the present invention. Broadwin is simply a pinpoint device in which at one moment the radio frequency coagulation can be occurring next to the fragmentation of tissues that are being caused to bleed by ultrasound for their removal. There is no human arm force capable of being applied and utilized simultaneously in Broadwin.

Martin (U.S. Pat. No. 5,728,090) teaches an apparatus for irradiating a living cell that it is simply a flexible balloon tip on the end of a catheter with a cluster of light-emitting diodes. It is non-rigid. It is expandable. It is filled by lipid fluid under high pressure, and is then called a diffuser. It contains mostly cooling fluid, and no extreme force could ever be used to move the device of Martin through any human tissue. Martin solely gives a temperature display for a light irradiation device.

Kulick (U.S. Pat. No. 5,425,355) is essentially a laser-energized device. Kulick tries to claim all forms of energy delivery for performing carpal tunnel or surgery in an extremely limited area. Kulick discloses limited area function repeatedly in the patent. Kulick effectively rules-out proximal manipulation of the instrument. Kulick states the exclusion of proximal side to side or up-down manipulation. Kulick is simply a combination of Farin, Kittrell, and Broadwin. Thus, Kulick cannot be used to undermine any large area in a planar fashion, as opposed to the present invention (which is capable of forcefully undermining a large area such as a face-lift). Kulick states this repeatedly. Although Kulick does contain a multiplicity of items, including laser energy delivering devices, air sources, "scopes" and suction, Kulick does not provide for the ability to maintain a tracking motion in a plane of tissue in order to efficiently separate or create a well defined plane. The Kulick delivery device is extremely similar to Farin and looks like a feminine product dispenser. The use of the Kulick device to undermine a breast capsule around an implant is not very similar to the undermining of a facelift, and the capsulotomy would be largely incomplete using the Kulick device. The present invention is not intended to work for breast surgery thus showing another difference. Kulick describes in column 3 the laparascope is the preferred monitoring device, thus implying a need for endoscopy. In Kulick, the energy-discharging fiber is arrayed parallel to the longitudinal axis of the probe. In column 3, Kulick again describes that there are constraints and that the procedure is limited to working in a tunnel. In column 4, Kulick refers to the device as the probe, thus in the singular sense, mentioning that it has at least one interior rigid or semi-rigid conduit that in no way can this create or cut a wide planar separation of tissue. In column 4, Kulick re-emphasizes the intention to work without proximal or side to side manipulation. Kulick admits being forcibly dangerous to tissue, and has developed a deployable shield, which would be a safety device to prevent damage. Lines 65 through 70 of Kulick states the shield effectively prevents discharged energy from affecting healthy nearby tissue not intended to be transected, incised, or treated. Kulick mentions more protective necessities, such as a mesh or reciprocating sleeve or balloon in column 5. Kulick states in column 5 that once the shield is deployed, it further restricts the use and movement of the machinery, as opposed to the present invention. Kulick further states in columns 5 and 6 that energy is hidden in the interior of Kulick that is encased. Kulick differs again from the present invention, in that in the present invention, energy-releasing elements are deliberately exposed, not encased for periodic exposure, and specifically planned for tissues to ride or contact adjacent. In Kulick, column 9, an internal serration that is mentioned, which is used to help clean the fiber, which functions only when some retraction made to Kulick. This is very similar to the effect that was described for the device of Farin, as was previously discussed. The internal serrations of Kulick should not be mistaken for the external alternating protrusions and recessions (alternating processions and recessions) that help maintain tracking and tissue spacing in the present invention. Kulick states in column 12, lines 24 through 30, that the device works only in constrained cavities, areas that are substantially non-manipulable, and that Kulick operates in areas where there is no appreciable side to side motion. Again, the present invention is virtually the opposite of each of these characteristics. In column 12, Kulick states being a single probe which would be inefficient compared with art currently in use today to perform facelifting. If Kulick were a double probe, Kulick would not fit or traverse face-lift tissues properly. Too much instrumentation would be required probing/procedure if Kulick were multiple probes. In column 13, Kulick states about a multi-channel probe, however it is still one single probe with multiple internal channels, and not multiple external protrusions/bulbs as in the present invention (nor multiple alternating processions/protrusions with recessions). In column 13, claim 4, Kulick claims a shielded device. This is opposed to the present invention, which does not need to be shielded and is deliberately made in exposure of tissues. Kulik in claim 2 states an optical device would be necessary, thus implying visualization. The present invention works totally differently and does not need or require or become aided by visualization. The present invention works on feel and size exclusion. Kulick claim 5 admits the inhibiting of side to side motion of said probe, and expounds upon areas of use. In claim 6, Kulick admits the need for optical fibers and visualization, totally different from the present invention. In claims 8 and 9, Kulick indicates the narrow nature of the field of the workable area in Kulick including breast implant surgery. In claim 10, Kulick extensively describes a shield as opposed to the present invention. In further Claims, Kulick restates the shield, the mesh, the probe, the balloon, and the narrow workable surgical field.

SUMMARY OF THE INVENTION

An object of the present invention is to provide an undermining device that can position lysing surfaces at a proper level for fibrous tissue lysing during a face-lift. It is a further object of the invention to provide quick and accurate face-lifting maneuvers. It is yet a further object of the invention to provide a surgical face-lifting device that easily maintains the proper dissection plane. Additionally, it has been shown that thermal effects to the collagenous (dermal, superficial platysma musculature and other) tissues of the face in the facelift plane can cause cosmetically desirable contraction of the dermal tissues with beneficial tightening of the facial tissues. The present invention is designed to bring controllable thermal effects to the intended target tissues principally by radiofrequency and optionally by ultrasonic means.

Thermal damage/change, caused by a laser, to the collagenous (dermal, superficial platysma musculature and other) tissues of the face in the facelift plane can cause cosmetically desirable contraction with beneficial tightening of the facial tissues has been documented in *Manual of Tumescent Liposculpture and Laser Cosmetic Surgery* by Cook R C and Cook K K, Lippincott, Williams, and Wilkins, Philadelphia ISBN: 0-7817-1987-9. It can be deduced that similar thermal effects derived from radiofrequency devices can also cause similar changes. Use of the present invention may controllably cause thermally related healing contraction of the target tissues thus allowing face lifting in younger patients without the removal or cutting-out of skin.

The present invention is a method and apparatus for face-lifting the human body using electrosurgery or similar radiofrequency technology with or without the combination of ultrasonic energy. Objectives of the invention include making the performance of face-lifting more rapid, more safe and providing uniform tissue tightening by controlled tissue heating due to predictable distancing/positioning of the target tissues from the cutting/heating/lysing segments and allowed by the chosen shape of the device tip.

The invention basically involves forcing a specially designed blunt object through tissue that excludes important structures (nerves, vessels) thus avoiding entanglement or trauma or indiscriminate cutting of critical structures. The same protrusions that exclude critical structures by virtue of their relationship to recessions also serve to position the depth of the present invention with respect to the lower dermis. Blunt undermining compacts the stronger, firmer, strands of collagen contained within even tissues as soft fat into thicker "bands" (some overly thick for uniform cutting). Disadvantageously for a face-lift, traditional blunt object undermining will force aside and compact septae causing incomplete lysis or freeing of the tissues. Also undesirably for face-lifting, purely blunt object traditional undermining will result in the indiscriminate/random motion/uncontrollable-slippage of the undermining device tip and thusly the undermining device through target tissue. Herein, we propose a specially shaped device that provides some of the desirable aspects of blunt undermining but also the precision to easily maintain the proper horizontal tissue plane while tracking through face-lift tissue easily creating linear straight paths. The instrument meanwhile uniformly cuts/lyses small manageable bundles of compacted fibrous strands gathered within the fibro-fatty tissue. Additionally, controllable heating of the cutting elements by radiofrequency (electrosurgery) will alter/appropriately-damage the facial collagen causing contraction and tightening upon healing.

The invention works with force from the surgeon's arm in the following manner. The present invention is forced/moved along the axis of the shaft but may move sideways only if the surgeon desires by altering direction of pressure on the handle. The protrusions/bulbs protrude and the lysing segments recede along that same axis. The spacing of the protrusions (bulbs) and recessions (lysing segments) maintains the tracking of the instrument. Tracking is instantly palpable by the surgeon and requires no monitor to know how the device is moving. If the distance between tip protrusions is too great, for example ½ inch then the device would wobble during tracking up to ½ inch. Both the number and spacing of protrusions in the present invention prohibit wobble or lateral (horizontal) slippage during forward thrusting of the instrument. Uniquely vertical slippage is prohibited as well. The width of the protrusions/bulbs maintains the correct distance between the lysing segments and the delicate underside of the superficial skin or dermis. The protrusions/bulbs literally sequester the active element that constitutes the lysing area which may be composed of radiofrequency elements, sharp cutting metal, or ultrasonically resonating materials. The principle of burning or traumatizing the lower dermis or the collagen within the upper SQ fat tissues has been shown to cause contraction (tightening) of facial tissues desirable in a face-lift.

In another approach, the protrusions and recessions are only visible from the front (horizontal thickenings and thinnings) and consist of thickenings and/or thinnings of the end portions of the segments. Thus tracking will still occur and the dimensions of the depth of the protrusions and recessions approaches 0.

The unique tip is comprised of alternating, but relatively symmetrical-across-a-midline, protrusions and recessions. The protrusions can be bulbous, geometric, etc. As long as the tips of the protrusions are able to push and compress tissues into the recessions (in which either sharp metal cuts, ultrasonic segments vibrates, electro-radio frequency cuts, or some other tissue-lysing mechanism occurs) the device of the present invention will succeed in creating a "protected" plane. This is the essence of the present invention: at least two processions surround at least one recessed area in which tissue is compressed, destroyed or cut as the device is moved forward.

The device of the present invention is to be used with or without direct or indirect visualization. For lower face-lifting the surgeon incises the skin in front of the ears and under the chin. Only the sense of feel is necessary for the surgeon to move the present invention through the tissue planes of the face. No scope or visualization is necessary or is required.

The present invention makes use of human force applied by the arm of the surgeon. The crucial motion of tracking through target tissues occurs via the dynamic of the alternating protrusions and recessions at the tip. Exclusion of vital structures and compression of tissues from the proper skin levels are caused by the novel tip shape. Lysing and alteration of collagen may be enhanced by ultrasonic or other vibrations energies and also help the device to move through altered tissue. The surgeon can palpably feel the device of tracking in the proper location. The "tracking" feel is instantaneous information for the surgeon. This "real time feel" is better than any screen or monitor and the feel of the present invention as it moves with palpable and easily gradeable resistance through the facial tissues can immediately tell the surgeon the location and the amount of undermining that has occurred at that location.

The radiofrequency or ultrasound energized device allows for the application of the energy of human force as the probes are forced through the tissue. Thus, three types of energy can be applied while the device is in motion, as opposed to some of the prior art that functions only while the devices are mostly stationary). The present invention is capable of delivering relatively strong human arm forces, which act in combination with other energies such as radio frequency, or ultrasonic, or other source of vibration for enhanced performance. Ultrasonic energy or resonance at lower hertz than ultrasonic may help clear the recessions of any debris or charred debris that may accumulate during device usage.

To resist the heat of the radiofrequency lysing segment (either a metal or conductive wire or bar) porcelain (heat-resistant) may constitute the protuberant/bulbous tip. The conductive/electrical wire passes through the bulbous porcelain tip that is connected to a shaft, which fits into a preexisting electrosurgical handpiece. The electrosurgical handpiece does not have to be preexisting, and could be entirely formed around the device as well. The handpiece rocker control can activate an electrosurgical generator to energize the handpiece tip, so that the target tissues can be controllably heated when tip of the device is forced through facial tissue. The controllably heated tissues will be precisely and purposefully altered thus causing fibrotic contraction during the healing period. The lysing head of the present invention could also dissipate energy at the tip thus altering the collagen and thereby causing the dermis (leather layer of the skin) to later contract during the healing period following a facelift.

The present invention of alternating tip protrusions is capable of being forcefully thrust through human tissue, yet in a very accurate and immediately palpable and appreciable fashion. Most importantly motion can be rapid linear and radial. The close spacing of the grooves (caused by the alternation of tip protrusions and recessions) provides the surgeon with a feel during forced tissue movement. Again, the tip of the device, and the action of the device can be felt/appreciated without visualization (scope). The purpose of the radiofrequency in the present invention may be to vaporize the tissue that impedes the uniform movement of the device, but most importantly to alter/irritate the collagen so as to cause later shrinkage and to control any bleeding. The purpose for optional ultrasound energy is to enhance the cutting/lysing tendency of the recessions between the protrusions so that the fibrous bands can be broken in the tissues that separate the subcutaneous tissue of the face from the dermis, or leather layer, of the face. The present invention, again, is capable of being forced through human tissue in a rapid and effective fashion allowing for facial contraction and undermining in literally five to ten minutes per side of face. The present invention is self-cleaning due to tissue abrasion and does not need to have the surface or treatment tips withdrawn in order to effect a cleaning. The movement of the present invention through target tissues causes compression and friction against the tip segments which will literally scrape off any char or tissue build-up, especially if a non-adherent polymer (such as silicon) may be attached or sprayed on the tip surface prior to the operation. The present invention allows the surgeon to work by "feel" which provides instantaneous knowledge of the progress of the lift and the location of the instrument thus the present invention does not require the use of a scope, monitor, or scanner to find out where the tip of our instrument is located.

Thus, a need exists for an improved face-lifting device that addresses the deficiencies of the prior art. The present invention circumvents the above-mentioned problems and provides a method for face-lifting the human skin with radiofrequency surgery with and without the aid of ultrasonic energy. Furthermore, it would be beneficial for the device to lift/separate such target skin easily, economically, and quickly, without pain or the risk of injury. The present invention provides a simple and economical process for human face-lifting, which can be used in hospital-based as well as office-based surgery.

Other objects, features, and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

FIG. 2 Shows a side view of face-lift apparatus.

FIG. 3 Enlarged view of upper face-lift apparatus tip.

FIG. 4 Enlarged view of lower face-lift apparatus tip.

FIG. 5 Enlarged partial cross-section of face-lift apparatus tip taken at 5—5 of FIG. 3.

DETAILED DESCRIPTION OF THE INVENTION

The following examples and accompanying drawings, which are incorporated into and form part of this disclosure, illustrate embodiments of the invention and together with the description, serve to explain the principles of the invention.

Figure 1:
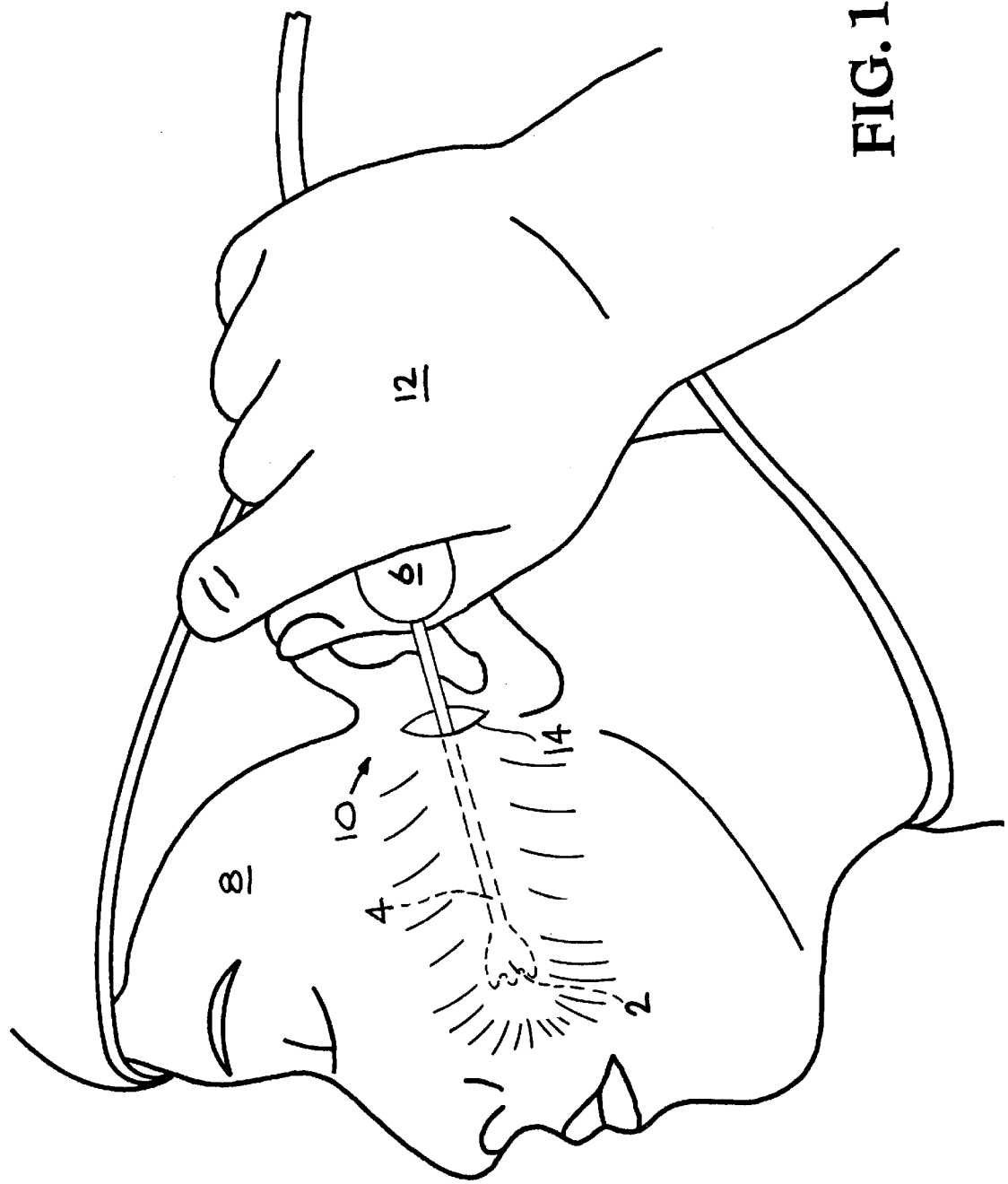
FIG. 1 Shows present invention (face lift apparatus) in use.

FIG. 1 shows the face-lift apparatus 10 of the present invention as it is being used. The handle 6 of the apparatus 10 is gripped in the hand 12 of the operator of the device. The shaft 4 with the attached tip 2 of the face-lift apparatus 10 is inserted through an opening at a suitable location on the face 8 of a patient. The apparatus may then be thrust forwardly while lifted forcefully by the operator to perform its function and maintain the plane of undermining.

FIG. 2 is a side view of the face-lift apparatus 10. The tip 2 may be slightly larger than the shaft 4 to which it is attached. The tip 2 can be secured to shaft 4 by a variety of methods such as a snap mechanism, mating grooves, plastic sonic welding, etc. The tip 2 is constructed of materials that are both electrically non-conductive and of low thermal conductivity; such materials might be porcelain, ceramics or plastics. The shaft 4 is tubular in shape or can be a somewhat flattened tube oblong in cross section. The shaft 4 is made of metal with a hollow interior that will contain insulated wire or wires 16. Alternatively, the shaft 4 may be made of plastic that will act as its own insulation about wire or wires 16. The wires 16 internal to shaft 4 conduct electrical impulses or RF signals from an electrosurgical handpiece 18 located in handle 6. These impulses are transmitted from a electrosurgical handpiece 18 to the tip 2. Electrical energy is transmitted from an external generator (such as a Valleylab Surgistat, Boulder, Colo.) through standard wiring to the electrosurgical handpiece 18. In the embodiment shown here in FIG. 2 the shaft 4 is interlocked with the handle 6. The handle 6 has a recess into which an electrosurgical handpiece 18 may be installed. As previously stated, the electrosurgical handpiece 18 allows control of electrical or RF impulses sent to tip 2. The electrosurgical handpiece has a power control switch 20 to control its function. A male/female connector 24 makes the connection between the electrosurgical handpiece 18 and the wires 16. The electrosurgical handpiece 18 is secured in handle 6 by door 22. The electrosurgical handpiece 18 receives its power from an external source or electrosurgical generator (source not shown in the figure). A temperature sensor 35 is placed near the energized section of the tip to monitor tissue temperatures in order to create feedback or audible output to the surgeon or a computer so as to controllably reduce the amount of radiofrequency or ultrasonic energy applied to the target tissues.

FIG. 3 is an enlarged plan or top view of the tip 2 as used in upper face-lift. This tip 2 shows five protrusions 26 and four recessions 28. The groove created by the tapering recessions may be noticeable up to one centimeter in length. The width W of this tip varies between 12 mm to 20 mm and the thickness varies between 3 mm to 4 mm. The tip, however, is not constrained by those dimensions. Also shown in FIG. 3 are the conductors 30 that transmit the signals supplied by wire 16 from electrosurgical handpiece 18 to tip 2. Connection between conductors 30 embedded in tip 2 and wires 16 in shaft 4 is made at the time tip and shaft are joined.

FIG. 4 is another enlarged plan or top view of a tip 2. This tip has three protrusions and two recessions and is the tip design used in lower face-lift. The width W of this tip varies between 5 mm and 10 mm while the thickness remains similar to the tip of FIG. 3 at 2 mm to 3 mm. This tip, however, is not constrained by those dimensions. Shown also are the conductors 30 for bringing power to the tip.

FIG. 5 is an enlarged partial cross section of a tip taken at 5—5 of FIG. 3. Here is shown the relationship between the protrusions 26 and the recessions 28. Also illustrated is the conductor 30.

Figure 6:
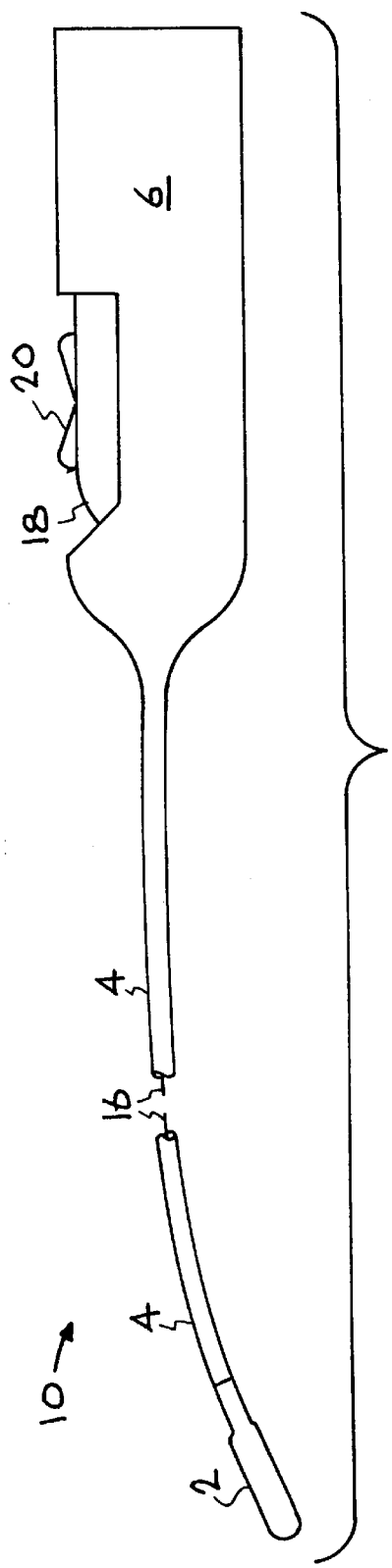
FIG. 6 Face lift apparatus with flexible shaft.

FIG. 6 is an illustration of a face-lift apparatus similar to those previously described. This apparatus differs in that shaft 4 is constructed of a material that allows shaft 4 to have some flexibility. This may reduce the stress to some patient's delicate skin during use. The shaft 4, however, must have enough rigidity to enable the operator to maintain control over positioning the tip 2.

Figure 7:
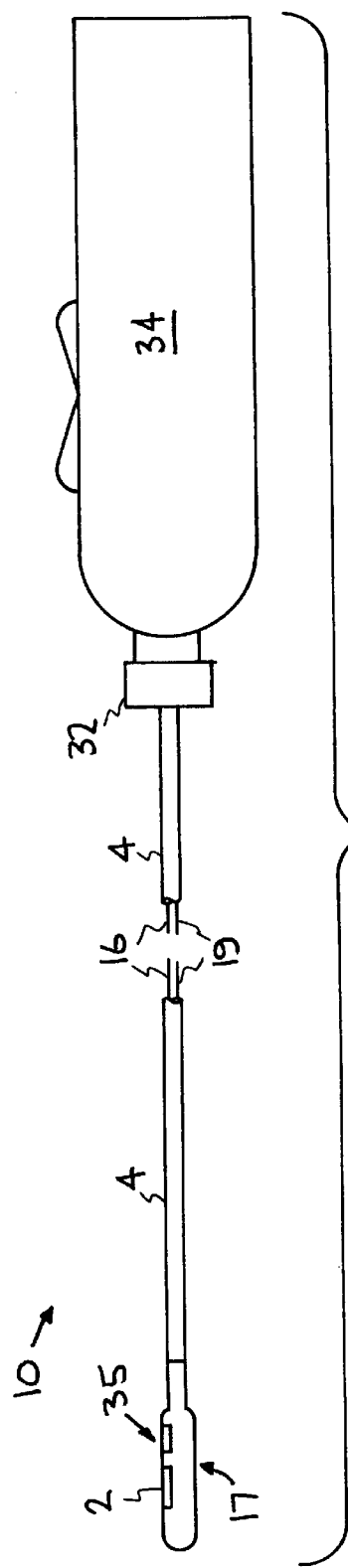
FIG. 7 Face lift apparatus with detachable shaft and electrosurgical handpiece integral with the handle.

FIG. 7 is a face-lift apparatus again similar to those previously described but differing in that the electrosurgical handpiece 18 and handle 6 have been combined to form integral unit 34. An optional and additional feature in the handle or hand-piece can be an ultrasonic piezoelectric transducer 32 that sends ultrasonic energy to the tip 2 of the face-lift device. The wire 16 would need to be replaced by a small metal shaft to conduct the ultrasonic energy. The shaft may be specially insulated or coated to protect surrounding tissue. Alternatively, to clear debris and to enhance efficiency a motor capable of lower vibrational energy may be incorporated into handle 34. Furthermore, uniform tissue heating element 17 may be incorporated on one side of the proximal tip and connected to insulated conductive element 19 passing through the shaft 4; 19 and thus 17 are controllably electrified at handle 34. It is noteworthy that radiofrequency uniform tissue heating element 17 that may be located on a side of the proximal tip or shaft is distinct and separate from the radiofrequency elements located in the lysing areas of the tip. It is also noteworthy that uniform tissue heating element 17 may be controlled in a fashion independent from the radiofrequency elements in the lysing segments. A temperature sensor 35 is placed near the energized section of the tip to monitor tissue temperatures in order to create feedback or audible output to the surgeon or a computer so as to controllably reduce the amount of radiofrequency or ultrasonic energy applied to the target tissues. This loop may thus controllably restrict thermal tissue damage and optimize contraction results. The temperature sensor 35 may be of an infrared type, optical fiber type, an electronic type, or optical fluorescence type, each being known in the prior art and thus a detailed description thereof is deemed unnecessary.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

What is claimed is:

1. An electrosurgical apparatus for separating facial subcutaneous tissue from dermal tissue, comprising;

a shaft having a distal end and a proximal end;

a plurality of protruding members on the distal end of the shaft separated by at least one interstitial lysing segment, wherein the lysing segment is recessed relative to the protruding members, and wherein at least one lysing segment comprises a conductive material such that said lysing segment also functions as an electrode, wherein said lysing segment is configured to separate facial tissue substantially in a plane; and means for delivering radiofrequency energy from the proximal end of the shaft to said lysing segment.

2. An apparatus as recited in claim 1, wherein at least a portion of the distal end of the shaft is formed of an electrically non-conductive material except for the lysing segment electrode.

3. An apparatus as recited in claim 2, wherein the non-conductive material is selected from the group consisting of plastics, graphite, graphite-fiberglass composites, ceramics, and glasses.

4. An apparatus as recited in claim 1, wherein the means for delivering radiofrequency energy comprises at least one insulated conductive member in the shaft.

5. An apparatus as recited in claim 1, further comprising means for delivering ultrasonic energy to the distal end of the shaft.

6. An apparatus as recited in claim 1, further comprising control means for controlling the delivery of radiofrequency energy to the distal end of the shaft.

7. An apparatus as recited in claim 6, further comprising a temperature sensor that senses the temperature at the distal end of the shaft, wherein the sensor sends a signal to the control means, and wherein the control means controls the delivery of radiofrequency energy to the distal end to adjust the temperature.

8. An apparatus as recited in claim 1, further comprising a temperature sensor.

9. An apparatus as recited in claim 8, wherein the temperature sensor comprises an infrared temperature sensor.

10. An apparatus as recited in claim 8, wherein the temperature sensor comprises an optical fiber temperature sensor.

11. An apparatus as recited in claim 8, wherein the temperature sensor comprises an electronic temperature sensor at the distal end of the shaft.

12. An apparatus as recited in claim 8, wherein the temperature sensor comprises an optical fluorescence sensor.

13. An apparatus as recited in claim 1, wherein the electrode is unipolar.

14. An apparatus as recited in claim 1, wherein the lysing segment comprises at least two electrodes, and wherein the means for delivering radiofrequency energy comprises at least two insulated conductive wires in the shaft, each wire connected to an electrode, and wherein the electrodes comprise a bipolar electrode.

15. An apparatus as recited in claim 1, wherein the thickness of the distal end of the shaft is less than about 1 cm and the width of the distal end is less than about 2 cm.

16. An apparatus as recited in claim 1, wherein at least one of the protruding members has an opening at the distal end.

17. An apparatus as recited in claim 1, further comprising at least one lumen extending through at least a portion of the shaft and terminating at the opening.

18. An apparatus as recited in claim 17, wherein lumen extending through at least a portion of the shaft and terminating at the opening is attached to a vacuum source.

19. The apparatus of claim 1, additionally including a handle which may contain an optional ultrasonic transducer piezoelectric and thus may impart ultrasonic energy to the shaft and thereby the tip.

20. The apparatus of claim 1, additionally including a handle which is composed of empty polyurethane or deformable or malleable or resilient plastic or polymer that can accommodate a standard electrosurgical handle.

21. The apparatus of claim 1, additionally including a handle capable of attaching to an electrosurgical generator for unipolar or bipolar functionality.

22. The apparatus of claim 1, wherein said distal end of the shaft is of a configuration selected from the group consisting of round or tapered.

23. The apparatus of claim 1, including a handle with a means that may impart vibrational energy to the shaft and thereby the tip.

24. The apparatus of claim 1, additionally including a radiofrequency means for uniform tissue heating, independently controlled and distinct from the radiofrequency means in the lysing segment.

25. The electrosurgical apparatus of claim 1, wherein at least one lysing segment comprises a cutting edge.

26. The electrosurgical apparatus of claim 1, wherein said lysing segment and said protruding members form a tip having a first cross-sectional area that is less than a second cross-sectional area of said tip that is about perpendicular to said first cross-sectional area.

27. An electrosurgical apparatus for separating facial subcutaneous tissue from dermal tissue, comprising:
- a shaft having a distal end and a proximal end;
- a plurality of protruding members on the distal end of the shaft separated by at least one interstitial lysing segment, wherein the lysing segment is recessed relative to the protruding members, wherein at least one lysing segment comprises a cutting edge;
- at least one electrode connected to said at least one interstitial lysing segment; and
- means for delivering radiofrequency energy from the proximal end of the shaft to the electrode in the lysing segment so that radiofrequency energy can be transmitted through the electrode.

28. An electrosurgical apparatus for separating facial subcutaneous tissue from dermal tissue, comprising:
- a shaft having a distal end and a proximal end;
- a plurality of protruding members on the distal end of the shaft separated by at least one interstitial lysing segment, wherein the lysing segment is recessed relative to the protruding members, and wherein at least one lysing segment comprises a cutting edge;
- at least one electrode connected to said at least one interstitial lysing segment; and
- means for delivering radiofrequency energy from the proximal end of the shaft to the electrode in the lysing segment so that radiofrequency energy can be transmitted through the electrode.

29. An electrosurgical apparatus for separating facial subcutaneous tissue from dermal tissue, comprising:
- a shaft having a distal end and a proximal end;
- a plurality of protruding members on the distal end of the shaft separated by at least one interstitial lysing segment, wherein the lysing segment is recessed relative to the protruding members, wherein said lysing segment and said protruding members form a tip having a first cross-sectional area that is less than a second cross-sectional area of said tip that is about perpendicular to said first cross-sectional area;
- at least one electrode connected to said at least one interstitial lysing segment; and
- means for delivering radiofrequency energy from the proximal end of the shaft to the electrode in the lysing segment so that radiofrequency energy can be transmitted through the electrode.

30. An electrosurgical apparatus for separating facial subcutaneous tissue from dermal tissue, comprising:
- a shaft having a distal end and a proximal end;
- a plurality of protruding members on the distal end of the shaft separated by at least one interstitial lysing segment, wherein the lysing segment is recessed relative to the protruding members, wherein said lysing segment and said protruding members form a tip having a first cross-sectional area that is less than a second cross-sectional area of said tip that is about perpendicular to said first cross-sectional area, wherein said lysing segment is configured to separate facial tissue substantially in a plane;
- at least one electrode connected to said at least one interstitial lysing segment; and
- means for delivering radiofrequency energy from the proximal end of the shaft to the electrode in the lysing segment so that radiofrequency energy can be transmitted through the electrode.

31. An electrosurgical apparatus for separating facial subcutaneous tissue from dermal tissue, comprising:
- a shaft having a distal end and a proximal end;
- a plurality of protruding members on the distal end of the shaft separated by at least one interstitial lysing segment, wherein the lysing segment is recessed relative to the protruding members, wherein said lysing segment and said protruding members form a tip having a first cross-sectional area that is less than a second cross-sectional area of said tip that is about perpendicular to said first cross-sectional area; and
- means for delivering radiofrequency energy from the proximal end of the shaft to said lysing segment.

32. An electrosurgical apparatus for separating facial subcutaneous tissue from dermal tissue, comprising:
- a shaft having a distal end and a proximal end;
- a plurality of protruding members on the distal end of the shaft separated by at least one interstitial lysing segment, wherein the lysing segment is recessed relative to the protruding members, and wherein at least one lysing segment comprises an electrically conductive cutting edge; and
- means for delivering radiofrequency energy from the proximal end of the shaft to said electrically conductive cutting edge.

* * * * *